United States Patent [19]

Hagen et al.

[11] Patent Number: 4,492,808
[45] Date of Patent: Jan. 8, 1985

[54] METHOD FOR SEPARATING ETHANOL FROM AN ETHANOL CONTAINING SOLUTION

[75] Inventors: Rainer Hagen; Jürgen Hartwig, both of Essen, Fed. Rep. of Germany

[73] Assignee: Fried. Krupp Gesellschaft mit beschränkter Haftung, Essen, Fed. Rep. of Germany

[21] Appl. No.: 600,301

[22] Filed: Apr. 13, 1984

[30] Foreign Application Priority Data

Apr. 14, 1983 [DE] Fed. Rep. of Germany ....... 3313530

[51] Int. Cl.³ .............. C07C 29/76; C07C 28/86; C07C 29/78; C07C 31/08
[52] U.S. Cl. .................. 568/916; 568/913; 568/917; 568/918; 435/161; 435/311
[58] Field of Search .......... 568/917, 918, 916, 913; 435/161, 311

[56] References Cited

U.S. PATENT DOCUMENTS

| | | | |
|---|---|---|---|
| 4,124,528 | 11/1978 | Modell | 252/411 |
| 4,260,836 | 4/1981 | Levy | 568/916 |
| 4,349,415 | 9/1982 | DeFilippi et al. | 568/918 |
| 4,358,536 | 11/1982 | Thorsson et al. | 435/161 |
| 4,359,593 | 11/1982 | Feldman | 568/916 |
| 4,376,163 | 3/1983 | Ehnstrom | 435/161 |
| 4,383,040 | 5/1983 | Fricker | 435/161 |

FOREIGN PATENT DOCUMENTS

2840440  3/1980  Fed. Rep. of Germany ...... 568/913

OTHER PUBLICATIONS

Kittur et al., "Proc. Indian Academy of Science", vol. IV A, p. 569 (1936).
Groszek, "Chemistry and Industry", pp. 1754–1756, (Oct. 15, 1966).

Primary Examiner—J. E. Evans
Attorney, Agent, or Firm—Spencer & Frank

[57] ABSTRACT

A process is disclosed for the separation of ethanol from an ethanol containing water solution, wherein the ethanol containing solution is extracted by means of a solvent which is in the liquid or supercritical state, the ethanol containing solvent phase is separated into its components by being conducted over an adsorption medium without changing the pressure or temperature, and the ethanol is recovered by treating the ethanol containing adsorption medium with the solvent used for the extraction at a pressure from 1 to 30 bar and at a temperature from 150° to 300° C.

11 Claims, 1 Drawing Figure

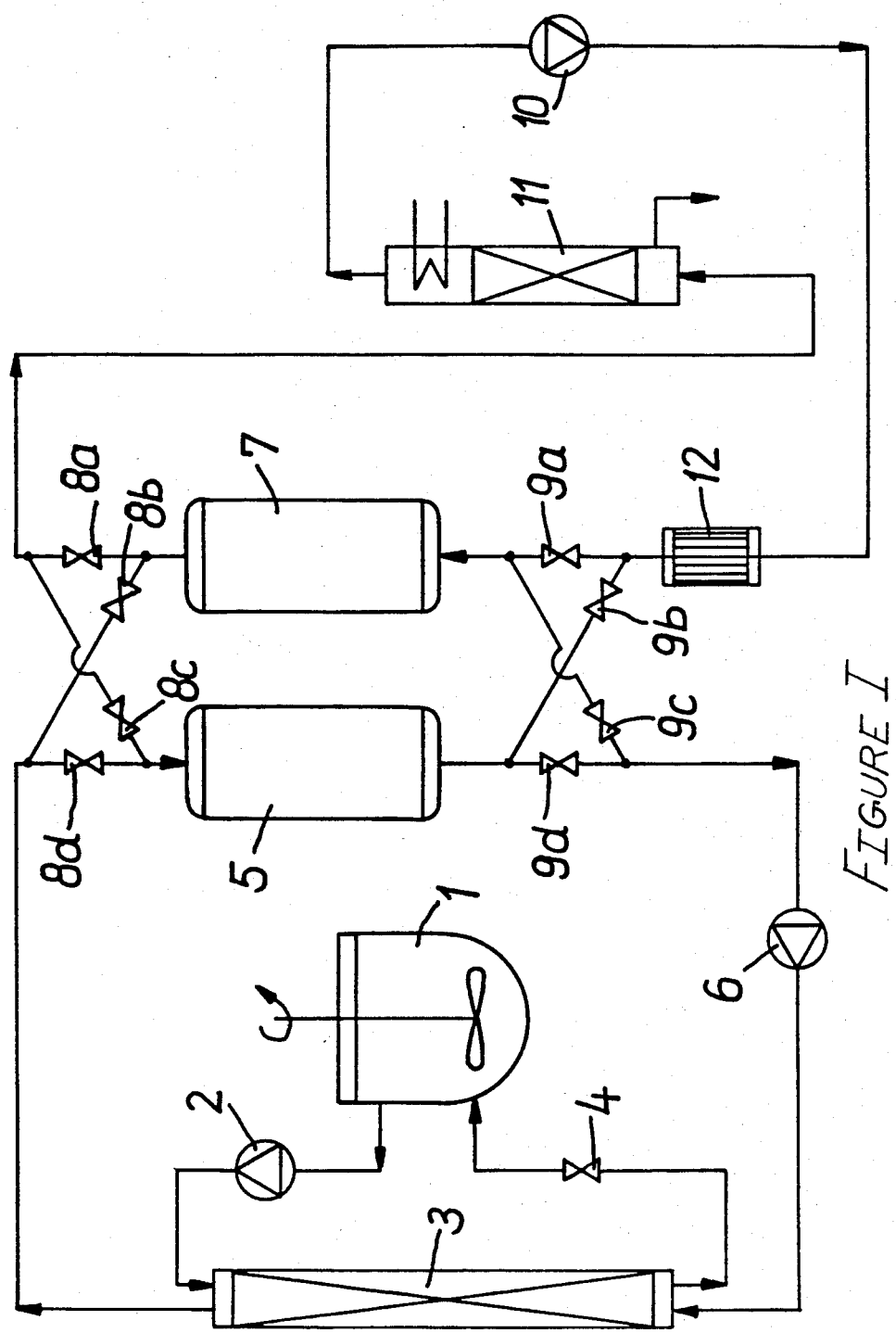
FIGURE I

METHOD FOR SEPARATING ETHANOL FROM AN ETHANOL CONTAINING SOLUTION

The present invention relates to a method for separating ethanol from the ethanol containing solution obtained during alcoholic fermentation, with the ethanol containing solution being extracted by a solvent that is gaseous at 20° C. and 1 bar and is in the liquid or supercritical state during the extraction process; wherein the ethanol containing solvent phase, after separation from the ethanol-poor solution, is fractionated into its components to recover the ethanol.

This invention may be used to recover ethanol from any ethanol-water solution.

BACKGROUND OF THE INVENTION

During alcoholic fermentation, sugar, particularly glucose, is separated into ethanol and carbon dioxide in the presence of yeast cells which contain the enzyme complex zymase. Glucose is produced by enzymatic splitting of maltose, which is itself formed during the hydrolytic, enzymatic splitting of starch or is developed during the manufacture of sugar. In addition to ethanol, the ethanol solutions developed during alcoholic fermentation contain soluble and insoluble components of vegetable cells and builders, yeast cells, starch and fractions of starch, various sugars, salts and water. The ethanol content of the solutions obtained during alcoholic fermentation is usually about 6 weight percent, since a higher ethanol concentration would reduce the reaction rate of the alcoholic fermentation too much.

Ethanol can be separated from the solutions obtained during alcoholic fermentation by means of distillation processes, and can be concentrated to a purity of 99.9 weight percent. However, distillation processes have the drawback that they require a large amount of energy. Distillation of up to an ethanol concentration of only 95 weight percent requires about 8000 kJ/kg of distillate, while the caloric value of ethanol is 26,780 kJ/kg. For concentrating beyond the azeotropic point, which for 1 bar lies at 95.58 weight percent ethanol, a considerable additional amount of energy is required. The high energy cost of ethanol separation by distillation is an economic impediment for using ethanol produced by alcoholic fermentation as an engine fuel.

To avoid the high energy costs for separating ethanol by distillation, ethanol can be separated from solution by means of extraction with a solvent. German laid-open patent application No. 3,033,729 discloses a method for separating ethanol from aqueous solution, wherein the ethanol containing solution is extracted with $CO_2$, $C_2H_4$ or $C_2H_6$ in the form of liquids or supercritical gases. If $CO_2$ is used as the extracting agent, the extraction can take place at 30 to 150 atmospheres and at 0° to 150° C. In this known process the pressure of the ethanol containing extract phase is reduced and the ethanol is separated from the extraction agent by distillation. A considerable amount of energy and a large amount of apparatus is required for processing the ethanol containing extract phase.

BRIEF DESCRIPTION OF THE INVENTION

It is, therefore, the object of the present invention to provide a process for separating ethanol from ethanol containing solutions, particularly ethanol solutions obtained during alcoholic fermentation, by extraction with a solvent followed by ethanol recovery, with a process requiring the least possible amount of energy and the minimum amount of apparatus.

This invention may be used to recover ethanol from any ethanol-water solution.

This is accomplished by the present invention by passing the ethanol containing solvent phase, without changing pressure or temperature, over an adsorption medium; returning the ethanol free solvent phase to the extraction stage; driving out the ethanol from the ethanol containing adsorption medium by treatment with the solvent used for extraction in the gas phase at a pressure of from 1 to 30 bar and at a temperature of from 150° to 300° C.; separating ethanol from the gas phase by cooling to below the boiling temperature of ethanol at the existing pressure to form a liquid ethanol phase and substantially ethanol free gas phase; and recirculating the substantially ethanol free gas phase. According to the process of the present invention, ethanol can be recovered from the solution obtained during alcoholic fermentation using an amount of energy which is approximately 50% of the energy required for the atmospheric distillation of ethanol to an ethanol concentration of 95 weight percent, and which is lower than the amount of energy required for separating a supercritical, ethanol containing gas by distillation. A further advantage of the process according to the present invention is that the energy balance is not adversely influenced by the occurrence of azeotropic mixtures. It is surprising that ethanol can be separated from the solvent phase using an adsorption agent under the pressure and temperature conditions existing during the extraction of ethanol from solution because, normally, liquid or supercritical gases are employed to regenerate charged adsorption agents, i.e. to separate the adsorbed substances from the adsorption agents (see U.S. Pat. No. 4,124,528).

DETAILED DESCRIPTION OF THE INVENTION

According the the present invention, it is provided that the extraction of ethanol from the ethanol containing solution and the adsorption of the ethanol from the ethanol containing solvent phase takes place at a temperature of from 0° to 200° C., preferably 20° to 100° C., and at a pressure of from 1 to 500 bar, preferably 20 to 250 bar, and that $C_2H_4$, $C_2H_6$, $C_3H_6$, $C_3H_8$, $C_4H_8$, $C_4H_{10}$, LPG, $CO_2$, $CF_3Cl$, $CF_3Br$, $C_2F_2Cl_2H_2$, $N_2O$ or a mixture of at least two of these substances is employed. It has been found that under these process conditions the ethanol can be advantageously recovered from the ethanol containing solution. According to the present invention, it is further provided that activated carbon, silica, magnesium oxide, silica gel or zeolites, preferably activated carbon in granulated or pelletized form, are employed as the adsorption medium; since with these adsorption media it is possible to substantially separate ethanol from the ethanol containing solvent phase.

For example, granulated activated carbon Nr. 72156 of the german firm Reininghaus with a size between 4 mm and 20 mm and an internal surface area of 1200 $m^2/g$ proved to be suited for the process. A substantially quantitative separation of ethanol from the adsorption medium is possible according to the present invention if 1 kg ethanol containing adsorption medium is treated with 3 to 25 kg, preferably 7 to 20 kg, of solvent. The process is able to produce ethanol with any concentration up to 100%.

The capacity of the adsorbent lies between 5 and 600 g ethanol per kg adsorbent, depending upon the nature of the solvent, the kind of the adsorbent, and the pressure and the temperature applied. For example, with $CO_2$ as a solvent 417 g ethanol/kg activated carbon (Reininghaus Nr. 72156) could be adsorbed at a pressure of 200 bar and a temperature of 75° C.

A particularly favorable, continuous alcoholic fermentation process to be used in conjunction with the process of the present invention is characterized by separating a partial stream of ethanol containing solution developed during alcoholic fermentation from the yeast cells by sedimentation or centrifugation. The yeast cell free partial stream is extracted and both the separated yeast cells and the ethanol free partial stream are returned to the alcoholic fermentation section. According to the present invention, the yeast cell separation step, before the extraction of ethanol from solution, can be omitted if a partial stream of the ethanol containing solution developed during alcoholic fermentation is extracted at 0° to 38° C. and is subsequently returned to the alcoholic fermentation section.

The present invention will now be described in greater detail with the aid of the following embodiment and FIG. I.

DESCRIPTION OF THE DRAWING

FIG. I is a process flow diagram for the process of the invention.

A particular stream of the solution obtained during alcoholic fermentation is continuously removed from fermenter 1, its pressure is raised to extraction pressure with pump 2, and it is conveyed at the head end into mass transfer column 3. In mass transfer column 3, the ethanol containing solution is extracted by the countercurrent flowing solvent. $C_2H_4$, $C_2H_6$, $C_3H_6$, $C_3H_8$, $C_4H_8$, $C_4H_{10}$, LPG (liquefied petroleum gas=$C_3$-, $C_4$-, $C_5$- hydrocarbons), $CO_2$, $CF_3Cl$, $CF_3Br$, $C_2F_2Cl_2H_2$, $N_2O$ or a mixture of at least two of these substances is used as the solvent. Particularly well suited are the solvents $C_2H_4$, $C_3H_6$, LPG or $CO_2$. Extraction of the ethanol containing solution is performed at a temperature of from 0° to 200° C., preferably 20° to 100° C., and at a pressure of from 1 to 500 bar, preferably 20 to 250 bar, with the weight ratio of solution to solvent ranging 1:3 to 1:10.

After extraction the ethanol poor solution leaves the bottom of mass transfer column 3, is depressurized via pressure reduction valve 4 to the operating pressure of fermenter 1, and is returned thereinto. Pressure reduction valve 4 may be connected to a separator vessel (not shown in FIG. I) in which the gaseous solvent is separated from the ethanol poor solution. The gaseous solvent may be returned to the extraction cycle. The ethanol poor solution may be returned to the fermenter, after degassing, or used for starting a mash with starch or sugar containing starting material.

The ethanol containing solvent phase leaves through the head of mass transfer column 3 and flows, without change in pressure or temperature, through vessel 5 which is filled with a bulk adsorption medium that adsorbs ethanol. The adsorption medium fill has little flow resistance since the adsorption medium is used in granular or pelletized form. After leaving vessel 5, the solvent phase is almost free of ethanol and it is conveyed by compressor 6 into mass transfer column 3. As soon as the adsorption medium contained in vessel 5 is charged with ethanol, vessel 5 is removed from the extraction cycle by appropriatly switching the blocking valves 8a through 8d and 9a through 9d, and the ethanol containing solvent phase is then conducted into vessel 7 which contains freshly regenerated adsorption medium that becomes charged with the ethanol.

Once the adsorption medium in vessel 5 has been saturated with ethanol and vessel 5 has been removed from the extraction cycle, superheated gaseous solvent, heated to desorption temperature in heat exchanger 12, is introduced into vessel 5 and extracts the adsorbed ethanol as well as small quantities of water. The ethanol containing gaseous solvent is then cooled in column 11 to below the boiling temperature of ethanol at the pressure within column 11, and is separated into its components. Liquid ethanol is removed from the bottom of column 11, while the substantially ethanol free gaseous solvent is conveyed by compressor 10 to heat exchanger 12. Due to the fact that the same substance is employed to initially extract ethanol from solution and to desorb the ethanol, it is not necessary to dry the adsorption medium.

It is possible to expand mass transfer column 3 by adding a rectifying section (not shown in the drawing) which is operated with a return flow of water containing ethanol originating from the regeneration cycle. The rectifying section is employed if the ethanol containing solvent phase contains too much water. The return flow in the rectifying section must contain enough water that these is a miscibility gap with the ethanol containing solvent phase.

EXAMPLE I

A partial stream having an ethanol content of 5.6 weight percent and a temperature of 38° C. is removed from fermenter 1 and is substantially freed from yeast cells and other solids in a sedimentation tank. The yeast containing sludge is extracted at the bottom of the tank and returned to fermenter 1. The ethanol containing, almost yeast free solution is heated to 75° C., compressed by pump 2 to a pressure of 80 bar, and conveyed into mass transfer column 3 where it is contacted in countercurrent flow with the ascending supercritical $CO_2$ phase, causing the ethanol to transfer drom the aqueous phase to the supercritical $CO_2$ phase. At the bottom of mass transfer column 3 the solution, which has been extracted to an ethanol concentration of 2.2 weight percent, is removed, its pressure is reduced to atmospheric pressure, it is degassed, and returned to the alcohol fermenter. The return of the ethanol-poor solution may be effected either by being directly fed to fermenter 1 or by being used to start a mash with the starch or sugar containing starting material.

The ethanol containing solvent phase travels from the head of mass transfer column 3 into vessel 5, where it flows at 75° C. and 80 bar over a fill of granulated activated carbon. The ethanol is adsorbed by the activated carbon while the $CO_2$ leaves vessel 5 and is returned, with the aid of compressor 6, into the sump of mass transfer column 3. As soon as the activated carbon is sataturated with ethanol it is treated, at 200° C. and 10 bar, with a stream of $CO_2$ which absorbs the ethanol as well as the residual water. The $CO_2$-ethanol mixture is fed into column 11 in which it is cooled to 75° C., causing the ethanol to liquefy so that it can be collected in the column sump with a residual water content of 1.5 weight percent. The $CO_2$ leaves through the head of column 11 and is heated to 200° C. in heat exchanger 12 and returned by compressor 10 to vessel 5 or vessel 7, respectively. During extraction, the quantity ratio between $CO_2$ and the ethanol containing solution is 7 kg $CO_2$ to 1 kg solution. The regeneration of 1 kg activated carbon requires 7.1 kg $CO_2$.

EXAMPLE II

A partial stream having an ethanol content of 6,5 weight percent and a temperature of 38° C. is removed from fermenter 1 and is substantially freed from yeast cells and other solids in a sedimentation tank. The yeast containing sludge is extracted at the bottom of the tank and returned to fermenter 1. The ethanol containing, almost yeast free solution is heated to 82° C., compressed by pump 2 to a pressure of 250 bar, and conveyed into mass transfer column 3 where it is contacted in countercurrent flow with the ascending supercritical $C_2H_4$ phase, causing the ethanol to transfer from the aqueous phase to the supercritical $C_2H_4$ phase. At the bottom of mass transfer column 3 the solution, which has been extracted to an ethanol concentration of 2,6 weight percent, is removed, its pressure is reduced to atmospheric pressure, it is degassed, and returned to the alcohol fermenter.

The ethanol containing solvent phase travels from the head of mass transfer column 3 into vessel 5, where it flows at 82° C. and 250 bar over a fill of granulated activated carbon. The ethanol is adsorbed by the activated carbon while the $C_2H_4$ leaves vessel 5 and is returned, with the aid of compressor 6, into the sump of mass transfer column 3. As soon as the activated carbon is staturated with ethanol it is treated, at 150° C. and 10 bar, with a stream of $C_2H_4$ which absorbs the ethanol as well as the residual water.

The $C_2H_4$-ethanol mixture is fed into column 11 in which it is cooled to 75° C., causing the ethanol to liquefy so that it can be collected in the column sump with a residual water content of 1,0 weight percent. The $C_2H_4$ leaves through the head of column 11 and is heated to 150° C. in heat exchanger 12 and returned by compressor 10 to vessel 5 or vessel 7, respectively. During extraction, the quantity ratio between $C_2H_4$ and the ethanol containing solution is 7 kg $C_2H_4$ to 1 kg solution. The regeneration of 1 kg activated carbon requires 3,2 kg $C_2H_4$.

Energy consumption in this example is about 4500 kJ/kg of product.

It will be understood that the above description of the present invention is susceptible to various modifications, changes and adaptations, and the same are intended to be comprehended within the meaning and range of equivalents of the appended claims.

What is claimed:

1. A process for separating ethanol from an ethanol containing water solution, wherein the ethanol containing solution is extracted in an extraction stage with a solvent that is gaseous at 20° C. and 1 bar and is in the liquid or supercritical state in the extraction stage, and wherein the ethanol containing solvent phase is separated from the ethanol poor solution after extraction and is then separated into its components to recover the ethanol; said ethanol recovery comprising the steps of: passing the ethanol containing solvent phase from the extraction stage without changing pressure or temperature over an adsorption medium and returning the ethanol free solvent phase to the extraction stage; driving out the ethanol from the adsorption medium with a gaseous extraction solvent stream at a pressure of 1 to 30 bar and at a temperature from 150° to 300° C.; cooling the gaseous extraction solvent which contains ethanol to below the boiling temperature of ethanol at the existing pressure to separate the stream into a liquid ethanol phase and a substantially ethanol free gas phase; and recirculating the substantially ethanol free gas phase.

2. The process of claim 1, wherein the extraction of ethanol from the ethanol containing solution and the adsorption of ethanol from the ethanol containing solvent phase take place at a temperature of from 0° to 200° C., and at a pressure of from 1 to 500 bar.

3. The process of claim 2, wherein the extraction of ethanol from the ethanol containing solution and the adsorption of ethanol from the ethanol containing solvent phase take place at a temperature of from 20° to 100° C., and at a pressure of from 20 to 250 bar.

4. The process of claim 1, wherein the solvent is selected from the group consisting of $C_2H_4$, $C_2H_6$, $C_3H_6$, $C_3H_8$, $C_4H_8$, $C_4H_{10}$, LPG, $CO_2$, $CF_3Cl$, $CF_3Br$, $C_2F_2Cl_2H_2$, $N_2O$, and a mixture of at least two of these substances.

5. The process of claim 1, wherein the adsorption medium is selected from the group consisting of activated carbon, silica, magnesium oxide, silica gel and zeolites.

6. The process as defined in claim 1, wherein the adsorption medium is activated carbon in granulated or pelletized form.

7. The process of claim 1, wherein each kg ethanol containing adsorption medium is treated with 3 to 25 kg of solvent.

8. The process of claim 1, wherein each kg ethanol codtaining adsorption medium is treated with 7 to 20 kg of solvent.

9. The process of claim 1, wherein the ethanol containing solution is produced during alcoholic fermentation.

10. The process of claim 9, wherein a partial stream of the ethanol containing solution obtained during alcoholic fermentation is settled or centrifuged to separate out yeast cells, the yeast free partial stream is extracted and the separated yeast cells as well as the ethanol poor partial stream are returned to the alcoholic fermentation.

11. The process of claim 9, wherein a partial stream of the ethanol containing solution obtained during alcoholic fermentation is extracted at 0° to 38° C. and is subsequently returned to the alcoholic fermentation.

* * * * *